United States Patent [19]

Torisu et al.

[11] 4,452,687

[45] Jun. 5, 1984

[54] LEANNESS SENSOR

[75] Inventors: Yoshio Torisu; Shigenori Sakurai; Takashi Kamo; Toshinobu Furutani, all of Toyota; Mari Okazaki, Chiryu, all of Japan

[73] Assignee: Toyota Jidosha Kogyo Kabushiki Kaisha, Toyota, Japan

[21] Appl. No.: 386,527

[22] Filed: Jun. 9, 1982

[30] Foreign Application Priority Data

Jun. 12, 1981 [JP] Japan .................................. 56-90624

[51] Int. Cl.³ ...................... G01N 27/58; G01N 27/30
[52] U.S. Cl. .................................... 204/428; 204/424; 204/425; 204/427
[58] Field of Search ............... 204/424, 425, 427, 428, 204/429

[56] References Cited

U.S. PATENT DOCUMENTS

| | | | |
|---|---|---|---|
| 3,841,987 | 10/1974 | Friese et al. | 204/427 |
| 3,941,673 | 3/1976 | Takao et al. | 204/427 |
| 4,049,524 | 9/1977 | Togawa et al. | 204/427 |
| 4,076,608 | 2/1978 | Fojishiro et al. | 204/427 |
| 4,157,282 | 6/1979 | Riddel | 204/428 X |
| 4,174,258 | 11/1979 | Bode | 204/424 |
| 4,189,355 | 2/1980 | Fujishiro et al. | 204/427 X |
| 4,199,425 | 4/1980 | Sinkevitch | 204/429 |
| 4,220,516 | 9/1980 | Sano et al. | 204/427 X |
| 4,328,295 | 5/1982 | Tanaka et al. | 204/424 X |
| 4,339,320 | 7/1982 | Friese et al. | 204/428 X |
| 4,347,113 | 8/1982 | Fischer et al. | 204/428 |
| 4,362,609 | 12/1982 | Sano et al. | 204/428 |

Primary Examiner—G. L. Kaplan
Assistant Examiner—Nam X. Nguyen
Attorney, Agent, or Firm—Oblon, Fisher, Spivak, McClelland & Maier

[57] ABSTRACT

A leanness sensor has a sensor element made of an oxygen-permeable solid electrolyte and having a cylindrical form or a form like a vessel closed at one end thereof. The sensor element is provided with metallic electrodes formed on the inner and outer surfaces thereof. An inner metallic member and an outer metallic member are mounted on the sensor element and electrically connected to the metallic electrodes. The sensor element is fixed to the inner side of the end portion of a cylindrical insulating tube.

7 Claims, 4 Drawing Figures

FIG. 1
FIG. 2
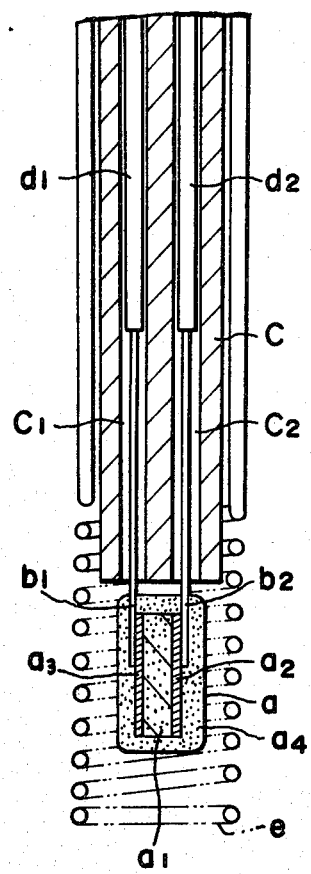
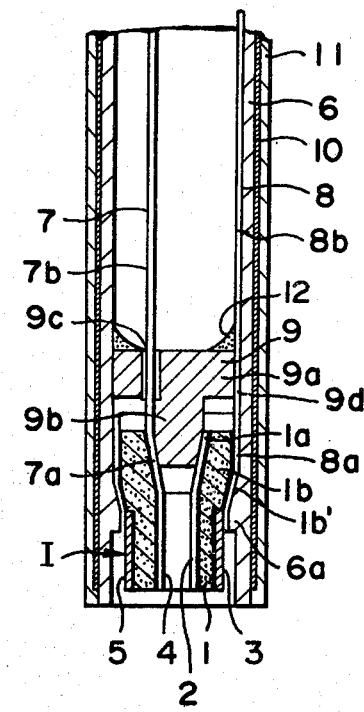

LEANNESS SENSOR

BACKGROUND OF THE INVENTION

1. Field of the Invention

This invention relates to a leanness sensor for detecting the oxygen concentration in a gas such as the exhaust gas from an internal combustion engine.

2. Description of the Prior Art:

Hitherto, there have been proposed various types of oxygen sensors capable of sensing the oxygen concentration in the exhaust gas of internal combustion engine. On oxygen sensor called a "leanness sensor", which has been developed as one of these known sensors, can detect the oxygen concentration in the exhaust gas over a wide range from low concentration up to a high concentration with accuracy in an order of several tenths of a percent.

The leanness sensor has a disc-shaped element made of a solid electrolyte permeable to oxygen ions, having metallic electrodes formed on both sides thereof. The operation of this leanness sensor is based upon oxygen permeating from one electrode (cathode) to the other electrode (anode) when a voltage is applied between these two electrodes. That is, a threshold current is generated in the element and limited by the flow rate of oxygen from the cathode, and the oxygen concentration in the exhaust gas is measured by continuously detecting the change of amplitude of the threshold current.

FIG. 1 shows the construction of a known leanness sensor. The leanness sensor has an element a including a disc-shaped main body $a_1$ made of zirconia stabilized by yttrium oxide or the like and electrodes $a_2$ and $a_3$, made of platinum or the like material, formed on both sides of the disc-shaped main body $a_1$. Lead wires $b_1$ and $b_2$ made of platinum or the like material are connected at their one ends to the electrodes $a_2$ and $a_3$. Porous protective layers $a_4$ made of alumina, spinel or the like material are formed on both sides of the element a. In order to limit the rate of transmission of oxygen, the electrode covering portions of the protective layers $a_4$ have different thicknesses on either side of the electrode in order to limit the rate of permeation by oxygen. The lead wires $b_1$ and $b_2$ extend through two bores $c_1$ and $c_2$ formed in an insulator tube c made from alumina or the like, and are connected to electric wires $d_1$ and $d_2$, so that the element a is fixed to the end of the insulator tube c by the lead wires $b_1$ and $b_2$. The element a is surrounded by a heater e made of nichrome wire or the like. In operation, the heater e is supplied with electric power to heat the element a up to the operating temperature.

The leanness sensor having the described construction, however, is unstable from a structural point of view because the sensor element a is fixed to and projects from the insulator tube c by means of lead wires $b_1$ and $b_2$. The lead wires $b_1$ and $b_2$ are usually made of thin platinum wires of a diameter less than 1 mm and therefore lack mechanical strength. In consequence, the lead wires $b_1$ and $b_2$ tend to become cut, causing various problems such as breakdown of the element a, detection failure for the element a and so forth.

Usually, the lead wires $b_1$ and $b_2$ are made of noble metals such as platinum. This inevitably raises the price of the leanness sensor.

SUMMARY OF THE INVENTION

Accordingly, one object of the invention is to provide a leanness sensor in which the detecting element has a cylindrical form so that the element can be rigidly secured to the insulator tube, to improve stability against impact.

Another object of the invention is to provide a leanness sensor in which the element has a cylindrical form and is provided with inner and outer metal members mounted on its inner and outer surfaces, so as to eliminate the necessity for use of precious platinum metals while achieving a stronger electric connection.

Still another object of the invention is to provide a leanness sensor having a cylindrical element so that the strength of the element itself is increased and the handling of the leanness sensor is facilitated.

The leanness sensor of the invention has a sensor element made of an oxygen permeable solid electrolyte having a hollow cylindrical form, or the form of a hollow cylindrical vessel closed at its one end. Metallic electrodes are formed on the inner and outer surfaces of the element main body. An inner metal member and an outer metal member are mounted in electric connection with the metallic electrodes. The sensor element is fixed to the inner side of one end of a cylindrical insulator tube.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several view, and wherein:

FIG. 1 is a sectional view of an essential part of a conventional leanness sensor;

FIG. 2 is a sectional view of an essential part of a leanness sensor in accordance with a first embodiment of the invention;

DETAILED DESCRIPTION OF THE PREFERRED EMBODIMENTS

Figure 3:
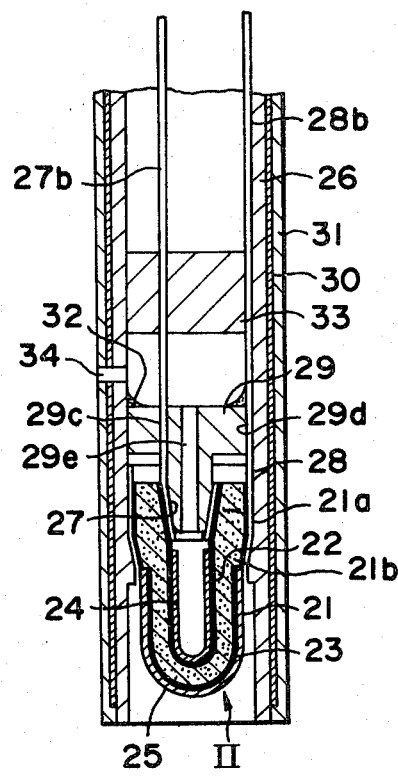
FIG. 3 is a sectional view of an essential part of a leanness sensor constructed in accordance with a second embodiment of the invention.

Leanness sensors of the invention will be described hereinunder with reference to the accompanying drawings.

FIG. 2 schematically shows the section of an essential part of a leanness sensor constructed in accordance with a first embodiment of the invention. The leanness sensor of the first embodiment has a leanness sensor element I consisting of a hollow substantially cylindrical element main body 1 opened at both ends and made of a solid electrolyte such as zirconia stabilized by yttrium oxide, and platinum electrodes 2 and 3 formed on the inner and outer surfaces of the element main body 1. An inner tapered portion 1a is formed on the inner peripheral surface of the substantially cylindrical element main body 1 at one open end of the latter so as to diverge towards the open end. On a portion of the outer peripheral surface of the inner tapered portion 1a, is formed a peripheral shoulder 1b extending radially outwardly.

The shoulder 1b has a stepped shape provided with a tapered portion 1b' which is narrowed in the direction of projection of the element body. Reference numerals 4 and 5 denote protective layers formed on the surfaces of the inner and outer platinum electrodes 2 and 3, said protective layers made of alumina and spinel and adapted to protect the electrodes and to limit the flow of oxygen through the cathode.

A cylindrical insulating pipe 6 is made of an insulating material having superior strength and resistance to heat, such as alumina. The insulating tube 6 is provided, in the inner peripheral surface of lower portion thereof, with a retaining portion 6a having a shape corresponding to that of the shoulder 1b of the element I. Reference numeral 7 designates an inner metallic member electrically connected to the inner electrode 2 of the element main body 1. The inner metallic member is formed by a tapered ring portion 7a corresponding in shape to the inner tapered portion 1a of the element main body 1, and an elongated lead portion 7b which extends in the axial direction from the larger diameter axial end of the ring portion 7a and is slightly curved in the circumferential direction. The inner metallic member 7 is made of a metallic material having high heat resistance and electric conductivity, such as stainless steel, and is intended for applying a voltage to the inner electrode 2 while receiving the output from the inner electrode 2.

A reference numeral 8 designates an outer metallic member electrically connected to the outer electrode 3 provided on the outer peripheral surface of the element 1. The outer metallic member 8 has a stepped ring portion 8a of a diameter which closely fits and covers the outer peripheral surface of the shoulder portion 1b of the element I, and an elongated plate-shaped lead portion 8b which extends axially from the circumferentially larger end of the stepped ring portion 8a and is slightly curved in the circumferential direction. The outer metallic member 8 is made of the same material as the inner metallic member 7 and contacts with the outer electrode 3 so as to apply a voltage to, and receive the output from, the outer electrode 3.

Reference numeral 9 designates a retainer member having a substantially T-shaped cross section and made of a heat resistant and electrically insulating material. The retainer member 9 consists of a thick-walled disc-shaped portion 9a having the same inner diameter as the insulating pipe 6 and a closing portion 9b projected from the center of the disc-shaped portion 9a. The extremity of the closing portion 9b has a tapered form which narrows towards the projecting direction. The arrangement is such that, when the aforementioned retainer member 9 is inserted in the pipe 6, the closing portion 9b just fits the tapered ring portion 7a of the inner metallic member 7. The disc-shaped portion 9a is provided at its portion corresponding to the outer peripheral surface of the closing portion 9b with a hole 9c which extends through the thickness of the disc-shaped portion 9a. Also, a notch 9d is formed at a portion of the outer peripheral end of the disc-shaped portion 9a so as to extend through the thickness of the same. The through hole 9c receives the lead portion 7b of the inner metallic member, while the notch 9d receives the lead portion 8b of the outer metallic member.

Reference numeral 10 designates a thin film layer of a heat resistant metal such as tungsten, platinum or the like, formed on the outer peripheral surface of the insulating tube 6, while a reference numeral 11 designates a protective layer formed on the outer periphery of the thin film layer 10. The thin film layer 10 produces heat when electric power is applied, so that layer 10 serves as a heater for heating the element I.

A reference numeral 12 denotes an inorganic adhesive adapted for fixing the retainer member 9 to the inner peripheral surface of the insulating tube 6.

The leanness sensor of the described embodiment is assembled in the following procedure. First, the element I is inserted into the stepped ring portion 8a of the outer metallic member 8 so as to fit the stepped ring portion 8a around the shoulder 1b while the inner metallic member 7 is fitted to the inner tapered portion 1a of the element I. Subsequently, the above-mentioned assembly is inserted from above into the insulator tube 6, which has been provided with the metal thin film layer 10 and the protective layer 11 formed on the outer peripheral surface thereof, until the stepped ring portion 8a of the outer metallic member 8 is brought into engagement with the retainer portion 6a of the insulating tube 6. Then, the retainer member 9 is inserted into the insulating tube 6 until the closing portion 9b fits into the inner tapered portion 1a of the element I. Needless to say, it is necessary to circumferentially locate the retainer member 9 such that the lead portions 7b and 8b are aligned with the through hole 9c and the notch 9d of the retainer member 9, respectively. After pressing and fitting the retainer member 9 to the tapered portion 1a of the element in the manner described, a heat resistant inorganic adhesive 12 is applied to the upper surface of the disc-shaped portion 9a of the retainer member 9 thereby to bond and fix the same. It is advisable to interpose an electrically conductive inorganic adhesive to the juncture between the outer shoulder of the element I and the retaining portion 6a of the insulating tube thereby to increase the bonding strength.

The leanness sensor of the described embodiment assembled in the above-mentioned procedure can detect a change in the electric current between the inner electrode 2 and the outer electrode 3 via the inner and outer metallic members 7 and 8. In addition, the element I is protected against impact and the bonding strength of the element I is improved because the element I is held in the insulating tube 6 by means of the metallic members 7 and 8.

FIG. 3 is a cross-section view showing an essential part of a leanness sensor constructed in accordance with a second embodiment of the present invention.

The lean sensor element II of this embodiment has an element main body 21 having a substantially cylindrical vessel-like form closed at one end. Platinum electrode layers 22 and 23 are formed on the inner and outer surfaces of the main body 21 and protective layers 24 and 25 cover the surfaces of the electrodes. After fitting an outer metallic member 28 to a shoulder portion 21b formed on the outer peripheral surface of the open end portion of the element II and then fitting an inner metallic member 27 to the inner tapered portion 21a formed in the inner peripheral surface at the open end of the element II, the element II is fitted to the internal bore of a cylindrical insulating tube 26 which is beforehand provided on its outer periphery with a metallic thin film 30 and a protective layer 31. Thereafter, a retainer member 29 having a substantially T-shaped cross-section is inserted from above into the insulating tube 26 to fit the opening of the element II, and then the retainer member 29 is fixed to the insulating tube 26 by means of an inorganic adhesive 32. Furthermore, a closure plug 33 is fitted above the retainer member 29. The retainer member 29 has a vent hole 29e extending therethrough along the longitudinal axis thereof. A vent hole 34 opens in the portion of the cylindrical body consisting of the insulating tube 26, metallic thin film 30 and the insulating layer 31, at a point between the retainer member 29 and the closure plug 33. Although the cylindrical body in the illustrated embodiment has only one vent hole in the insulating tube 26, it is possible to provide two or more such vent holes. The lead portions 27b and 28b of the inner metallic member 27 and the outer metallic member 28 are extended to the outside through the through bore 29c and the through groove 29d which are formed in the retainer member 29 along the length of the latter.

In the leanness sensor of the second embodiment having the described construction, the gas to be detected is introduced through the lower opening of the insulating tube 26 and contacts the outer electrode of the sensor element II. Meanwhile, the gas to be detected is also introduced through the vent hole 34 and the vent hole 29e to contact the inner electrode of the element II. The element II is isolated from the atmosphere by the closure plug 33.

Figure 4:
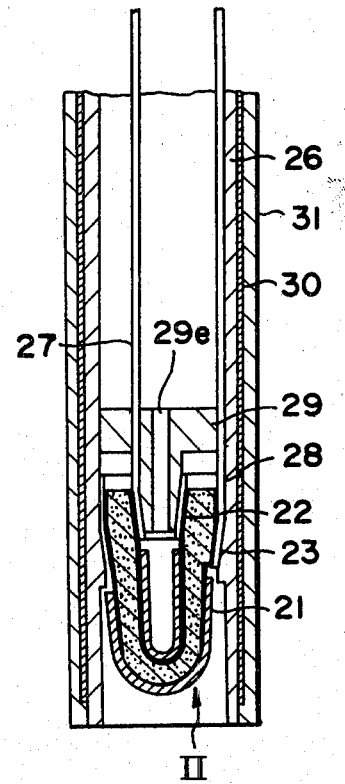
FIG. 4 is a sectional view of an essential part of a leanness sensor constructed in accordance with a third embodiment of the invention.

FIG. 4 is a cross-section view showing an essential part of a leanness sensor in accordance with a third embodiment of the present invention. This leanness sensor has a construction substantially the same as that of the second embodiment except that the inner side of the sensor element II is allowed to communicate with the atmosphere. Therefore, the side wall of the insulating tube 26 has no vent hole, and the closure plug above the retainer member 29 is eliminated. In the leanness sensor of the third embodiment, the gas to be detected contacts the outer electrode 23 of the element II and the change in the electric current flowing between the outer electrode and the inner electrode is measured as the output signal. The inner side of the element II is communicated with the atmosphere through the vent hole 29e provided in the retainer member 29.

In each of the leanness sensor elements of the embodiments described heretofore, the protective layers covering the inner electrode and the outer electrode have respectively different thicknesses so that a threshold current is generated in the element. This threshold current is transmitted to the outside through the inner and outer metallic members and measured as the oxygen concentration in the gas to be measured. The threshold current in the element may be generated by differentiating the areas of the electrodes, materials of the electrodes and the like measure, instead of differentiating the thickness of the electrode protective layers as in the embodiments described hereinbefore.

In the illustrated embodiments, the retainer member has a substantially T-shaped cross-section such that the outer peripheral surface of the disc portion thereof contacts the inner peripheral surface of the insulating tube as illustrated in the drawings, thereby to increase the strength of fixing of the element. The retainer member, however, may be substituted by a plug member which has a through bore and a through groove for merely holding the lead portions of the inner and outer metallic members. In such a case, the sensor element is attached to the insulating tube by applying an adhesive to the outer surface of the shoulder portion of the element.

As will be clearly understood from the foregoing description, in the leanness sensor of the present invention, the sensor element has a cylindrical or a vessel-like form, and is mounted in the insulating tube through heat-resistant and electrically conductive metallic members connected to the electrodes of the element. In consequence, the strength or rigidity of attaching of the sensor element is increased and, hence, the stability against impact is remarkably improved as compared with the conventional leanness sensor in which the disc-shaped element is held merely by lead wires connected to both sides thereof. In addition, since the shoulder portion of the sensor element and the retaining portion of the insulating tube are made to engage with each other and strongly bonded by an adhesive or fixed by the retainer member to rigidly fix the sensor element to the insulating tube, the requirement for the oxidation resistance of the metallic members themselves for applying voltage and picking up the output is not so severe. This in turn eliminates the necessity for use of precious metals such as platinum which has been essential in the conventional leanness sensors. In consequence, the production cost is lowered and the natural resources are saved advantageously.

Obviously, numerous modifications and variations of the present invention are possible in light of the above teachings. It is therefore to be understood that within the scope of the appended claims, the invention may be practiced otherwise than as specifically described herein. What is claimed as new and desired to be secured by Letters Patent of the United States is:

1. A leanness sensor comprising:
    a sensor element formed of element main body made of an oxygen-permeable solid electrolyte and being provided with inner and outer metallic electrodes respectively formed on the inner and outer surfaces of the element main body;
    a retainer member having a substantially T-shaped cross section including a tapered closing portion;
    an inner metallic member and an outer metallic member mounted on said sensor element and electrically connected to respective inner and outer metallic electrodes; and
    a cylindrical insulating tube, said sensor element being fixed to the inside of one end of said insulating tube,
    wherein said sensor element is provided on the inner peripheral surface of an open end thereof with a tapered portion diverging radially outwardly towards said open end, said tapered closing portion of said retainer member being fitted in said tapered portion of said sensor element for securing said sensor element, and a radially outwardly projecting shoulder portion formed on the radially outer periphery of said open end,
    wherein said cylindrical insulating tube is provided in the inner peripheral surface at said one end thereof with a retaining portion projected therefrom and having a form corresponding to that of said shoulder of said sensor element.

2. A leanness sensor as claimed in claim 1 wherein said sensor element has a hollow cylindrical form opened at both ends thereof.

3. A leanness sensor as claimed in claim 1 wherein said sensor element has a hollow vessel-like form closed at one end thereof.

4. A leanness sensor as claimed in claim 1 wherein said cylindrical insulating tube is made of an inorganic alumina insulating material having superior mechanical strength and heat resistance.

5. A leanness sensor as claimed in claim 1, wherein each of said inner and outer metallic members has a ring portion for engaging and enclosing one of said tapered portion and said shoulder formed on said open end of said sensor element, and a lead portion.

6. A leanness sensor as claimed in claim 1, wherein each of said inner and outer metallic members is made of a heat-resistant stainless steel.

7. The leanness sensor of claim 1 wherein said retainer member is bonded to said insulating tube in a position such that it secures said sensor element to said insulating tube.

* * * * *